United States Patent
Axo et al.

(10) Patent No.: US 11,602,287 B2
(45) Date of Patent: Mar. 14, 2023

(54) AUTOMATICALLY AIDING INDIVIDUALS WITH DEVELOPING AUDITORY ATTENTION ABILITIES

(71) Applicant: International Business Machines Corporation, Armonk, NY (US)

(72) Inventors: Stefania Axo, Highland, NY (US); Mark Christopher Wallen, Highland, NY (US); Keith Joseph Miller, Pawling, NY (US); Yang Liu, Yorktown Heights, NY (US); Richard Polhemus, Lagrangeville, NY (US)

(73) Assignee: International Business Machines Corporation, Armonk, NY (US)

( * ) Notice: Subject to any disclaimer, the term of this patent is extended or adjusted under 35 U.S.C. 154(b) by 452 days.

(21) Appl. No.: 16/835,831

(22) Filed: Mar. 31, 2020

(65) Prior Publication Data
US 2021/0298647 A1   Sep. 30, 2021

(51) Int. Cl.
*A61B 5/12* (2006.01)
*H04R 1/10* (2006.01)
(Continued)

(52) U.S. Cl.
CPC .......... *A61B 5/125* (2013.01); *A61B 5/165* (2013.01); *A61B 5/4836* (2013.01);
(Continued)

(58) Field of Classification Search
CPC .... H04R 5/033–0335; H04R 25/00–75; H04R 2201/10–405; H04R 2225/00–83;
(Continued)

(56) References Cited

U.S. PATENT DOCUMENTS

| 6,882,971 B2 | 4/2005 | Craner |
| 7,340,393 B2 | 3/2008 | Mitsuyoshi |
| (Continued) | | |

FOREIGN PATENT DOCUMENTS

| CN | 1455916 A | 11/2003 |
| CN | 102184661 B | 9/2011 |
| CN | 203790136 U | 8/2014 |

OTHER PUBLICATIONS

Dunn, "Google works out a fascinating, slightly scary way for AI to isolate voices in a crowd," Ars Technica; Apr. 13, 2018; URL: https://arstechnica.com/gadgets/2018/04/google-works-out-a-fascinating-slightly-scary-way-for-ai-to-isolate-voices-in-a-crowd/; Retrieved on Mar. 20, 2020; 7 pages.
(Continued)

*Primary Examiner* — Thaddeus B Cox
(74) *Attorney, Agent, or Firm* — Cantor Colburn LLP; Tihon Poltavets

(57) ABSTRACT

Aspects include identifying each of a plurality of audio sources proximate to a user wearing a headset. The audio sources include a primary audio source and a plurality of background audio sources. Aspects include causing the headset to play a set of audio sources to the user by causing each audio source of the set to be unfiltered by the headset. Aspects include determining an acceptance level of the user. Aspects also include determining a background noise filtering adjustment based on the acceptance level and the set of audio sources being played by the headset to the user. Aspects also include causing the headset to adjust a filtering of one or more of the plurality of background audio sources by the headset based on the background noise filtering adjustment.

19 Claims, 6 Drawing Sheets

(51) Int. Cl.
*A61M 21/00* (2006.01)
*A61B 5/16* (2006.01)
*A61B 5/00* (2006.01)

(52) U.S. Cl.
CPC .......... *A61B 5/6803* (2013.01); *A61B 5/7267* (2013.01); *A61M 21/00* (2013.01); *H04R 1/1041* (2013.01); *A61B 5/0077* (2013.01); *A61M 2021/0027* (2013.01)

(58) Field of Classification Search
CPC ........... H04R 2430/00–25; H04R 2460/00–17; H04R 1/10–1091; A61B 5/165–168
See application file for complete search history.

(56) References Cited

U.S. PATENT DOCUMENTS

| | | | |
|---|---|---|---|
| 8,494,507 | B1 | 7/2013 | Tedesco et al. |
| 8,804,918 | B2 | 8/2014 | Jaiswal et al. |
| 9,031,293 | B2 | 5/2015 | Kalinli-Akbacak |
| 9,460,715 | B2 | 10/2016 | Hart et al. |
| 10,362,385 | B1* | 7/2019 | Di Censo ............. H04R 1/1091 |
| 11,234,073 | B1* | 1/2022 | Xu .................. G10K 11/17857 |
| 2015/0099946 | A1 | 4/2015 | Sahin |
| 2015/0195641 | A1* | 7/2015 | Di Censo ............. H04R 1/1083 381/71.6 |
| 2016/0323666 | A1* | 11/2016 | Ajmera ..................... H04S 7/30 |
| 2018/0336000 | A1* | 11/2018 | Vaughn ................ H04R 1/1083 |
| 2019/0013003 | A1* | 1/2019 | Baughman ........... H04R 29/001 |
| 2020/0030151 | A1* | 1/2020 | Hemberg ............. H04R 1/1083 |
| 2020/0125317 | A1* | 4/2020 | Sabin ..................... H04R 1/406 |
| 2020/0128322 | A1* | 4/2020 | Sabin ..................... G06F 3/012 |
| 2021/0306771 | A1* | 9/2021 | El Guindi ............ A61B 5/6815 |

OTHER PUBLICATIONS

Wikipedia, "Heuristic," Wikipedia.org; URL: https://en.wikipedia.org/wiki/Heuristic; Retrieved Mar. 20, 2020; 9 pages.
Wikipedia, "Hyper-heuristic," Wikipedia.org; URL: https://en.wikipedia.org/wiki/Hyper-heuristic; Retrieved Mar. 20, 2020; 8 pages.
Wikipedia, "Independent component analysis," Wikipedia.org; URL: https://en.wikipedia.org/wiki/Independent_component_analysis; Retrieved Mar. 20, 2020; 14 pages.
Wikipedia, "Machine learning," Wikipedia.org; URL: https://en.wikipedia.org/wiki/Machine_learning; Retrieved Mar. 20, 2020; 22 pages.

* cited by examiner

AUTOMATICALLY AIDING INDIVIDUALS WITH DEVELOPING AUDITORY ATTENTION ABILITIES

The present invention generally relates to computer processing systems, and more specifically, to automatically aiding an individual with developing auditory attention abilities.

In recent times, researchers have gained a better understanding of why those living with conditions such as attention deficit disorder (ADD) or autism have difficulty processing language by studying the so-called "Cocktail Party Effect," which refers to an individual's ability to tune in or to focus their attention on one person's voice amidst background noise that creates interference and difficulty in hearing the voice. Studies of brain activity suggest that individuals without ADD or autism generally have the ability to filter out extraneous noises in order to focus on a selected person's voice, whereas individuals that have these conditions often have difficulty in doing so.

SUMMARY

Embodiments of the present invention are directed to automatically aiding an individual with developing auditory attention abilities. A non-limiting example of the computer-implemented method includes identifying each of a plurality of audio sources proximate to a user wearing a headset. The plurality of audio sources includes a primary audio source and a plurality of background audio sources. The method also includes causing the headset to play a set of audio sources to the user by causing each audio source of the set of audio sources to be unfiltered by the headset. The set of audio sources includes the primary audio source and a first group of background audio sources of the plurality of background audio sources. A second group of background audio sources of the plurality of background audio sources are filtered by the headset. The method also includes determining an acceptance level of the user. The method also includes determining a background noise filtering adjustment based at least in part on the acceptance level and the set of audio sources being played by the headset to the user. The method also includes causing the headset to adjust a filtering of one or more of the plurality of background audio sources by the headset based at least in part on the background noise filtering adjustment.

Other embodiments of the present invention implement features of the above-described method in computer systems and computer program products.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
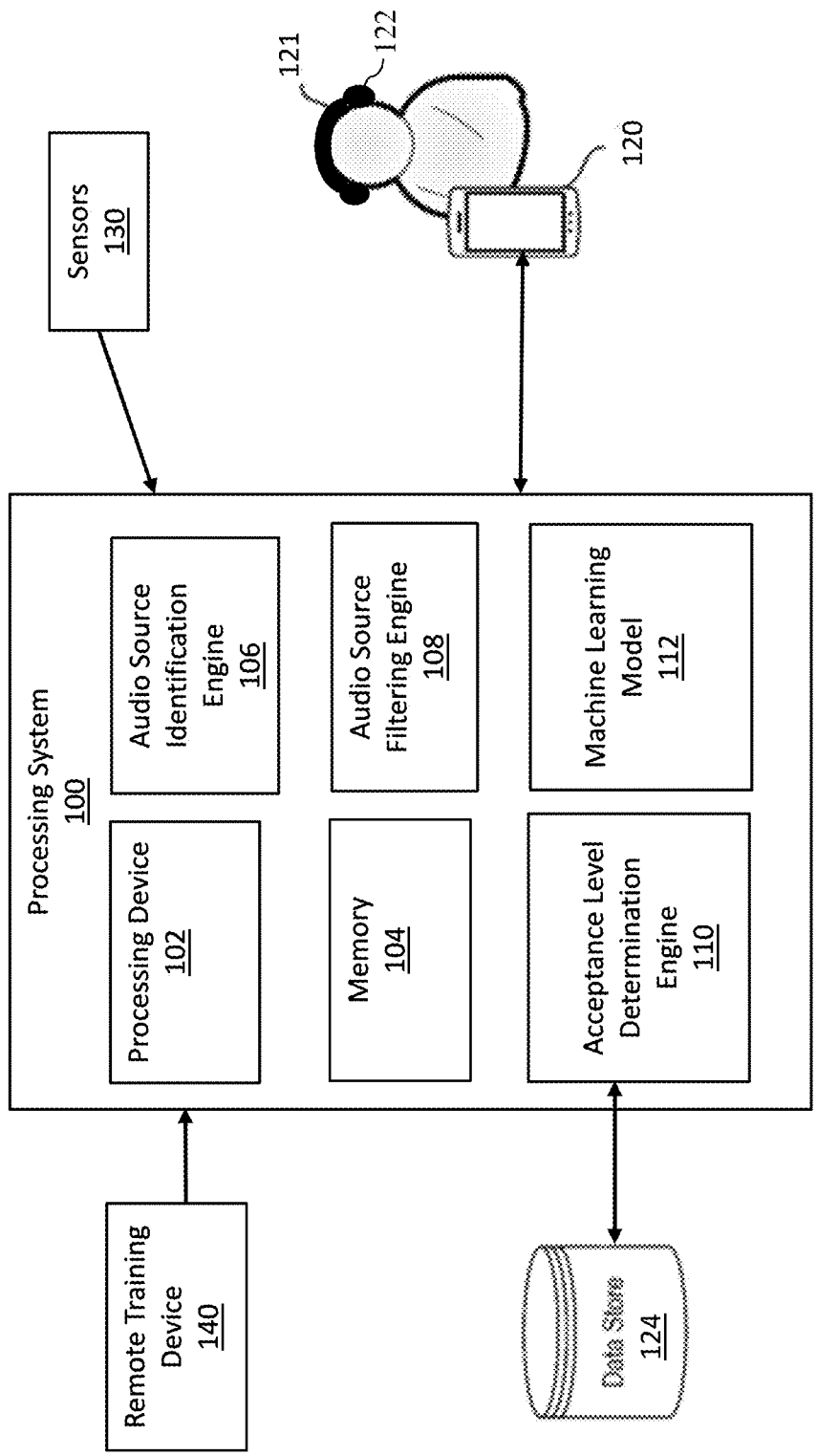
FIG. 1 depicts a system upon which automatically aiding an individual with developing auditory attention abilities may be implemented according to one or more embodiments of the present invention.

The diagrams depicted herein are illustrative. There can be many variations to the diagrams or the operations described therein without departing from the spirit of the invention. For instance, the actions can be performed in a differing order or actions can be added, deleted or modified. Also, the term "coupled" and variations thereof describe having a communications path between two elements and do not imply a direct connection between the elements with no intervening elements/connections between them. All of these variations are considered a part of the specification.

DETAILED DESCRIPTION

As described above, individuals with conditions such as attention deficit disorder (ADD) or autism can have difficulty in tuning in or maintaining focus on a selected person's voice in situations where there is a lot of background noise. Various audio sources such as different individuals speaking, music or television noise, cell phones ringing, dogs barking, cars honking, or any other type of background noise can combine to create what may be referred to as a "cocktail" of sounds that mix together in a manner that makes it difficult for those with ADD or autism to isolate and focus on a particular target audio source (e.g., a particular voice). Those without these conditions are generally better able to utilize what is known as the "cocktail effect," which is an ability to mentally "tune out" background noise and focus in on one audio source. For example, if an individual is talking to a friend at a loud party, the individual can use the cocktail effect to hear what the friend is saying, despite all of the interference to the friend's voice signal presented by the background noise.

As will be appreciated, an inability or difficulty in being able to utilize the cocktail effect can present great challenges in the lives of those who have these conditions, as it can be more difficult to follow or interact with others in situations that involve many people talking such as classrooms, work environments, social gatherings or other such situations with many people and/or much background noise. Therefore, it is desirable to provide technology for aiding such individuals in developing auditory attention abilities. Prior solutions to aid in dealing with a cocktail of sounds have been proposed, such as for example a hearing aid that allows dynamic selection of a preferred direction of hearing by the user based on the use of multiple microphones that identify the direction of sounds. Other prior methods have included providing modification of auditory streams to aid a user with autism spectrum disorder in better extracting meaning from the auditory stream. These contemporary approaches are directed towards aiding a user to improve their focus and understanding in a current situation, and not with aiding the user in developing their own natural ability to apply the cocktail effect.

One or more embodiments of the present invention address one or more of the above-described shortcomings of the prior art by providing techniques for automatically aiding an individual with developing auditory attention abilities by using machine learning to help the individual to manage and improve their ability to utilize the cocktail effect. Embodiments of the present invention can involve the use of noise-cancelation technology (e.g., noise-canceling headphones) in real-time settings (e.g., a live classroom setting) to filter out enough background audio sources to allow the user to adequately focus their auditory attention on a desired audio source (e.g., a teacher's voice) so that the user can successfully participate in the real-time activity. Embodiments of the present invention can also be used in a practice environment to help the user practice and better develop the ability to utilize the cocktail effect.

In accordance with one or more embodiments of the present invention, a machine learning model is used to automatically dynamically adjust which of the background audio sources that are present in the user's environment are canceled by a headset worn by the user based on the user's current state of acceptance of the present cocktail of sounds. In other words, if the user is struggling to focus on the primary audio source, the machine learning model can dynamically remove one or more sources of background noise from the cocktail of sounds to provide the user with less distraction. Conversely, if the user is tolerating the current level of background noise without difficulty, the machine learning model can dynamically adjust the level of background noise to add previously filtered audio sources to the cocktail of sounds to subject the user to a greater level of background noise. In this way, embodiments of the disclosure can aid the user in learning to develop their auditory attention abilities. The machine learning model can be individualized to a particular user so that training and development can be optimized for the user, based on the user's particular sensitivities. Use of an individualized machine learning model to dynamically adjust the cocktail of sounds provides technical advantages of providing background noise adjustments to facilitate auditory attention development in real-time, which can be used not only in training environments, but in everyday situations such as a student attending class at school.

Turning now to FIG. 1, a system 100 for automatically aiding an individual with developing auditory attention abilities is generally shown in accordance with one or more embodiments of the present invention. The various components, modules, engines, etc. described regarding FIG. 1 can be implemented as instructions stored on a computer-readable storage medium, as hardware modules, as special-purpose hardware (e.g., application specific hardware, application specific integrated circuits (ASICs), application specific special processors (ASSPs), field programmable gate arrays (FPGAs), as embedded controllers, hardwired circuitry, etc.), or as some combination or combinations of these. According to aspects of the present disclosure, the engine(s) described herein can be a combination of hardware and programming. The programming can be processor executable instructions stored on a tangible memory, and the hardware can include the processing device 102 for executing those instructions. Thus, a system memory (e.g., memory 104) can store program instructions that when executed by the processing device 102 implement the engines described herein. Other engines can also be utilized to include other features and functionality described in other examples herein.

The processing system 100 includes the processing device 102, the memory 104, an audio source identification engine 106, an audio source filtering engine 108, an acceptance level determination engine 110 and a machine learning model 112, which perform functionalities described in greater detail below. The processing system 100 can be configured to communicate with a user device 120, headphones 122, data store 124, sensors 130 and remote training device 140 via a communications network that may be one or more of, or a combination of, public (e.g., Internet), private (e.g., local area network, wide area network, virtual private network), and may include wireless and wireline transmission systems (e.g., satellite, cellular network, terrestrial networks, etc.). Alternatively, or in addition, such communications can be achieved using short range wireless communications technologies, such as for example Bluetooth, near-field communication (NFC), Wi-Fi, or another other such known wireless communication method. According to some embodiments, wired communications can also be employed to enable communications between devices (e.g., user device 120 can have a wired connection to headphones 122). The user device 120 can display data to and receive user inputs from a user 121, such as a user-input indication of how well the user is able to hear or focus on a primary audio source. In some embodiments, the remote training device 140 can allow another user (e.g., a parent, doctor, teacher or the like) to interact with processing system to manually select a given audio source as a primary audio source and to add/remove (i.e., unfilter/filter) one or more audio sources being played to the user 121 via the headphones. According to some embodiments, a user of remote training device 140 may cause one or more pre-recorded audio sources to be played to the user 121 as part of the audial cocktail presented to the user via the headphones 122. For example, during a training phase of the machine learning model, artificial (i.e., pre-recorded) sounds may be selected and played to the user 121 via the remote training device 140 to observe the user's 121 reactions. It will be understood that in some embodiments, such artificial sounds can be played to user 121 automatically at the direction of the processing system 100 as a part of training a machine learning model and/or providing the user 121 with an opportunity to practice focusing their attention on the primary audio source amidst background noise. Thus, it will be understood that in addition to filtering/unfaltering live audio sources to aid an individual with developing auditory attention abilities, it is also contemplated that in some embodiments, the system can similarly allow the user 121 to practice developing their auditory attention abilities through the use of artificial/pre-recorded sounds (either alone or in combination with live audio sources) that are played to the user 121 and adjusted in a similar manner as described herein with respect to live audio sources.

Figure 6:
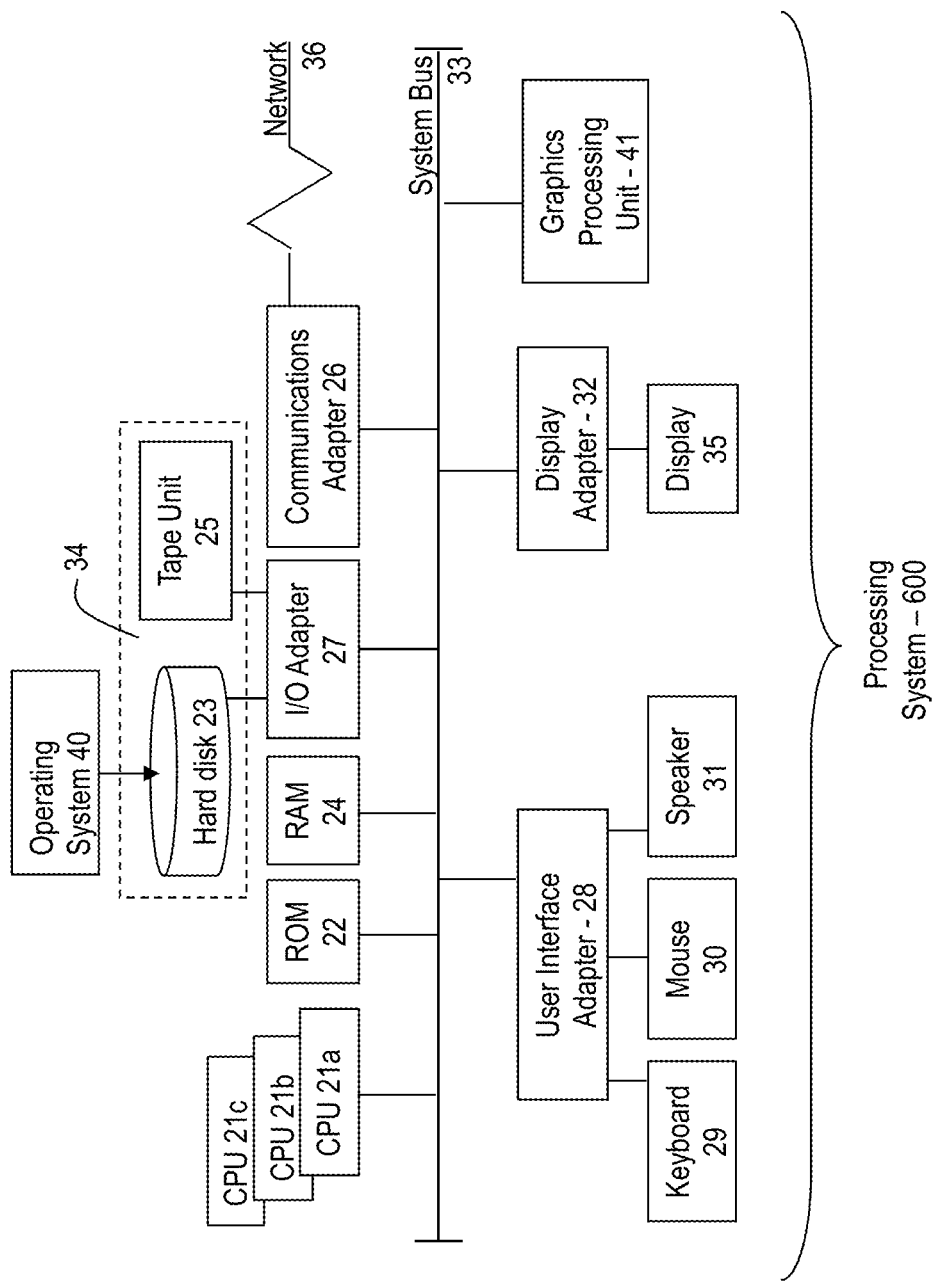
FIG. 6 illustrates a block diagram of a computer system for use in implementing one or more embodiments of the present invention.

In exemplary embodiments, user device 120 and/or remote training device 140 can be, but are not limited to, a desktop computer, a laptop, a tablet, a smartphone, a wearable device such as a smartwatch, an augmented reality headset, a tablet, a computer system such as the one shown in FIG. 6, or any other suitable electronic device. Data store 124 can be used to store some or all of the data needed to execute the functionalities of the processing system 100 described herein. In some embodiments, the data store 124 can store sound recordings (e.g., multiple recordings of different voices having conversations and other background sounds) that can be artificially introduced to the user 121 via headphones 122, for example, in response to a user input on remote training device 140. Although FIG. 1 depicts processing system 100 as being a separate device from user device 120, it should be understood that it is contemplated that in some embodiments, processing system 100 can be incorporated into user device 120. For example, user device 120 can execute a mobile application that performs all of the functions of processing system 100 and that can be directly and wirelessly connected to headphones 122.

According to some embodiments, headphones 122 can be noise-cancelling headphones that are configured to filter out selected audio sources as at the direction of the processing system 100, while allowing selected unfiltered audio sources to be played through to the user. For example, in a classroom setting, the headphones 122 can allow the teacher's voice to be played to a user 121 wearing the headphones 122 while filtering out one or more voices of other individuals in the classroom. Thus, for example, if the user 121 is in a crowded room with many people talking, the headphones 122 can cancel out the voices and/or other sounds in the room such that only a selected voice is played to the user 121. As will be appreciated by those of skill in the art, noise-canceling headphones can be configured to emit an anti-noise signal to contrast external sounds. While this disclosure generally refers to headphones 122, it should be understood that any device that is capable of performing a noise canceling functionality to filter out selected audio sources and/or sounds can be used, such as for example, systems that employ Internet-of-Things (IoT) microphones about the environment to record ambient sounds that are transmitted to a device worn by the user 121 (e.g., an ear piece) that can then produce a noise-canceling signal as the ambient sounds reach the user 121.

According to some embodiments, sensors 130 can include one or more sensors that are disposed proximate to user 121 or are otherwise positioned in a manner to observe and obtain sensor data from user 121. In some embodiments, sensors 130 can include one or more cameras that are positioned to observe the user's 121 facial expressions and/or body language. Sensors 130 can also include one or more biometric sensors, such as a heart rate monitor to measure the user's 121 heartrate, a microphone to record sounds from the user (e.g., sounds of exasperation, heavy or fast breathing, and the like), an optical sensor that is configured to track the user's gaze, and any other type of sensor that may be useful in obtaining information about that user can be used to assist in determining the user's acceptance level of the current level of background noise in the cocktail of sounds. Other aspects of processing system 100 will be described in greater detail below in reference to FIG. 2.

Figure 2:
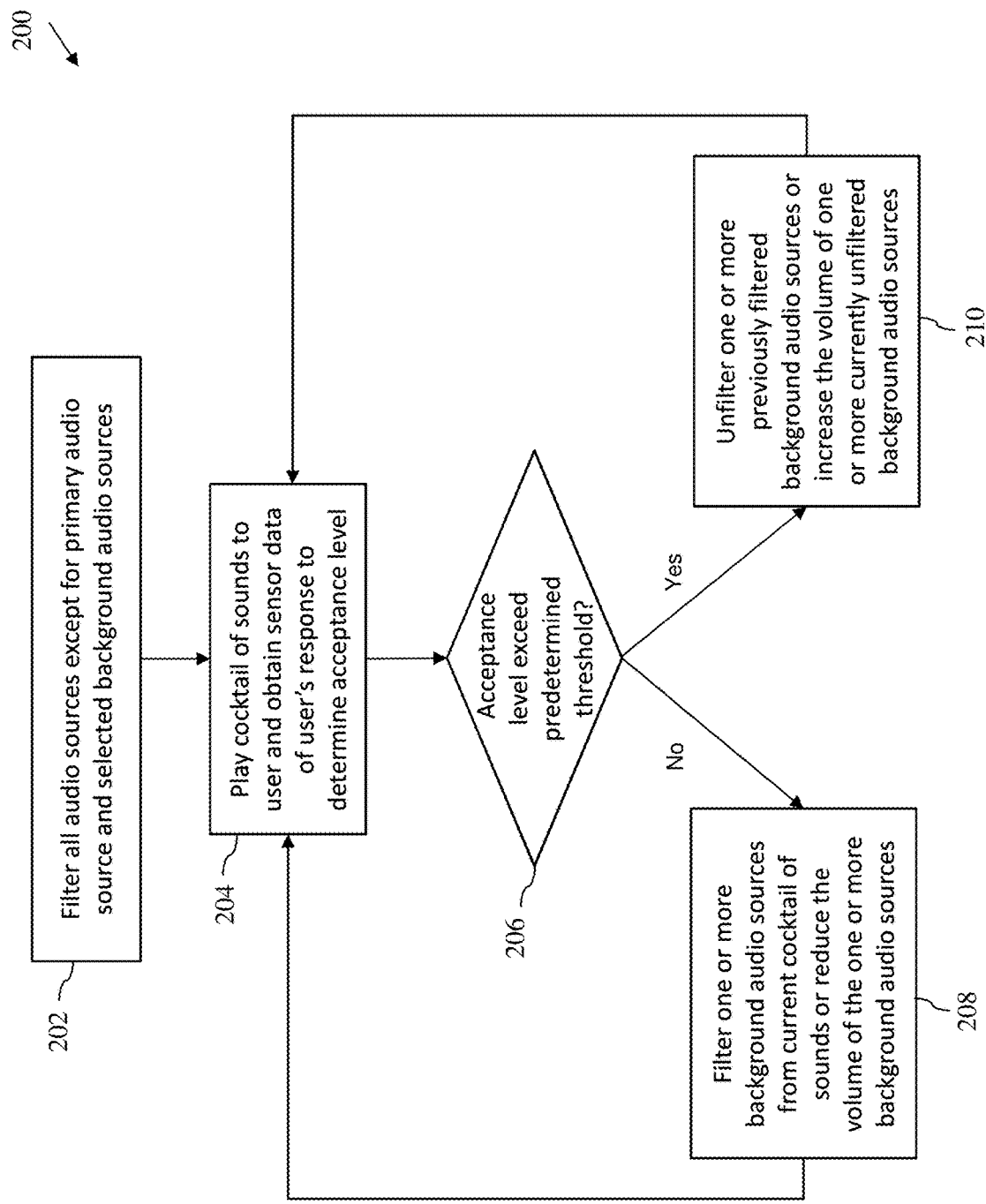
FIG. 2 illustrates a flow diagram of a process for automatically aiding an individual with developing auditory attention abilities in accordance with one or more embodiments of the present invention.

Turning now to FIG. 2, a flow diagram of a method 200 for automatically aiding an individual with developing auditory attention abilities in accordance with an embodiment is shown. In one or more embodiments of the present invention, the method 200 may be embodied in software that is executed by computer elements located within a network that may reside in the cloud, such as the cloud computing environment 50 described herein above and illustrated in FIGS. 4 and 5. In other embodiments, the computer elements may reside on a computer system or processing system, such as the processing system 100 described herein above and illustrated in FIG. 1, the processing system 600 illustrated in FIG. 6, or in some other type of computing or processing environment.

It will be understood that the environments in which method 200 is advantageously applied generally involve the user 121 being proximate to multiple nearby audio sources (e.g., individual voices, background music, traffic sounds, or any other such possible sources of background noise) that would typically give rise to use of the cocktail effect, such as for example but not limited to, a student being in a noisy classroom or an individual being in a crowded mall food court or any other such environment with significant background noise and/or many people talking at once. According to some embodiments, it is contemplated that one or more sensors 130 are disposed in the environment and/or about the person of user 121 to provide observations and readings about user 121 to processing system 100. For example, one or more video cameras, microphones, biometric sensors or other such sensors can be disposed about a room (e.g., a classroom) in a manner configured to take readings about the user 121 and surrounding environment, such as recording facial expressions of the user 121, picking up sounds made by the user 121, other people and other sources of noise within the environment, and/or taking biometric readings from the user, such as heartrate, respiration rate, temperature, movements made by the user 121, and any other such biometric readings that can be used to determine the user's 121 state of agitation. It is contemplated that user 121 would be wearing headphones 122, which are configured to filter out selected of the ambient/nearby audio sources at the direction of processing system 100. For example, it will be appreciated that noise-canceling headphones can filter/cancel out all ambient sounds except specific audio sources that have been selected to be unfiltered to allow the user to hear them.

The method 200 begins at block 202 and includes filtering (e.g., via processing system 100) all audio sources except for a primary audio source and selected background audio sources. The primary audio source refers to an audio source that the user 121 desires to focus on. For example, in a classroom setting, the primary audio source may be the teacher's voice, whereas in a crowded mall setting the primary audio source may be a friend or family member's voice. Background audio sources can be any audio source other than the primary audio source, that potentially creates interference with the primary audio source, which can result in the user 121 having difficulty focusing their auditory attention on the primary audio source such that, for example, the user 121 cannot follow what is being said by the primary audio source.

According to some embodiments, audio source identification engine 106 can receive one or more audio feeds from one or more sensors 130 (e.g., one or more microphones) within the environment of the user 121 and based on the one or more audio feeds, can automatically identify and/or distinguish one or more audio sources represented in the audio feed. For example, one or more microphones in a classroom may record ten different people talking at once, a sound of a radio playing and a sound of a dog barking from outside the classroom. According to some embodiments, using known techniques, such as combining auditory and visual signals of one or more input videos to separate the speech, Independent Components Analysis, or use of heuristic and statistic methods to combine audio and visual inputs to separate the audio sources, the audio source identification engine 106 can parse out the different audio sources and identifying that there are twelve different audio sources. In some embodiments, the audio source identification engine 106 can use additional sensor data from sensors 130 to identify one or more audio sources, by for example, using utilizing a video feed from smart camera to assist with separating out different voices in the room by comparing the movement of various individuals mouths to the sounds detected by microphones in the environment. As will be appreciated by those of skill in the art, Independent Components Analysis is a known process for decomposing a multivariate signal into independent non-Gaussian signals, and has been used to separate underlying speech signals from sample data. The audio source identification engine 106 can be configured to identify the audio sources using conventional methods such as determining that the frequency ranges of various signals correspond to known frequency ranges for humans, particular animals, devices or other known sources of sound, using known artificial intelligence techniques, using heuristic and statistic methods or any other technique that may be known or discovered. An example heuristic that could be use can be determining that a person is talking based on an observation that the person's mouth is moving (e.g., using known image recognition/analysis techniques to determine a person's mouth is opening and closing).

Thus, continuing with the previous example, the audio source identification engine 106 may identify that, for example, ten of the twelve audio sources are human voices, one is music and one is a dog. In some embodiments, the audio source identification engine 106 can associate a label with each identified audio source, such as for example "Human 1", "Human 2", "Dog 1", etc. In some embodiments, audio source identification engine 106 can identify a particular individual associated with a voice based on historical voice data stored by the system and change the label to represent the individual (e.g., "John Doe" instead of "Human 1"). A list of audio sources that have been identified by audio source identification engine 106 can be transmitted to and displayed by user device 120 and/or remote training device 140 for viewing by the user 121 or others. According to some embodiments, a human operator (e.g., user 121 or a user of remote training device 140) can manually change a label associated with an audio source via a software application of user device 120 and/or remote training device 140. Thus, one or more audio sources can also be identified and labeled by a user of the system. Furthermore, according to some embodiments, a primary audio source can be selected by the user 121 of user device 120 and/or a user of remote training device 140 by inputting a selection of one of the audio sources from the list. For example, if the user 121 is in a crowded mall and is interested in focusing on a first friend's speech, the user 121 can designate the first friend as the primary audio source, however if the user 121 decides they want to change their focus to a second friend, the user 121 can then designate the second friend as the primary audio source. According to some embodiments, the primary audio source can be designated by a third party (e.g., a user of remote training device 140), can be designated automatically by processing system 100 based on a context (e.g., a determination of who the user 121 is facing and engaging in conversation with), or can be preselected based on the nature of the environment (e.g., a teacher in a given classroom is preselected as the primary audio source).

According to some embodiments, audio source filtering engine 108 can be configured to selectively filter one or more identified (or unidentified) audio sources based an instruction from, for example, the machine learning model 112. In some embodiments, the audio source filtering engine 108 can receive selection of audio sources to filter or alternatively a selection of audio sources to unfilter. It will be understood that when an audio source is filtered it means that that audio source will be blocked/canceled by headphones 122 such that user 121 cannot hear the audio source. Conversely, it will be appreciated that when an audio source is unfiltered, it not blocked/canceled by the headphones 122 and is allowed to play through to the user 121 so that the user 121 can hear it. For example, if a teacher (i.e., a primary audio source) and three students (i.e., three background audio sources) are all talking at the same time and the audio source filtering engine 108 has received an instruction to filter the three students and unfilter the teacher, then the audio source filtering engine 108 will cause the headphones 122 to only play the sound of the teacher to the user 121, while canceling out the sounds of the three students. In this way, even though the user 121 may be within earshot of the three students, the headphones 122 will cause the user 121 to only be able to hear the teacher, thereby allowing the user 121 to focus on the voice of the teacher without interference or distraction. According to some embodiments, the headphones 122 can be configured to cancel all sounds except sounds transmitted to the headphones 122 from the audio source filtering engine 108, such that the audio source filtering engine 108 transmits the filtered audio signal to the headphones 122 to play to the user. However, in some embodiments, the filtering may be performed by the headphones 122 such that the audio source filtering engine 108 can instead transmit a list of filtered/unfiltered audio source designations to the headphones 122 and the headphones 122 filter the signals accordingly. The audio source filtering engine 108 can dynamically change which audio sources are filtered and which audio sources are unfiltered based on, for example, instructions from machine learning model 112 as described below.

As shown at block 204, the method includes playing (e.g., via headphones 122) a cocktail of sounds (i.e., a mix of one or more unfiltered audio sources) to the user 121 and obtaining sensor data (e.g., from sensors 130) of the user's 121 response to the cocktail of sounds to determine the user's acceptance level. As described previously above, in some embodiments, the audio source filtering engine 108 can provide a filtered audio signal or a list of selected audio signals to filter and/or unfilter to headphones 122, which can play the unfiltered audio sources to the user 121 while blocking/canceling out the filtered audio sources.

As the user 121 listens to the cocktail of sounds, the user 121 will attempt to focus their auditory attention on the primary audio source. For example, if the cocktail of sounds includes a teacher's voice (i.e., the primary audio source) and three students (i.e., three background audio sources) all talking at the same time, the headphones 122 will play all four audio sources to the user 121 and the user will attempt to focus on the teacher's voice and for example, follow along with a lesson that is being taught. In some instances, the user 121 may be able to focus well on the teacher's voice, whereas in other instances the user 121 may struggle to focus on the teacher's voice due to the distraction/audial interference presented by the voices of the three students. It will be understood by those of skill in the art, that an individual that is struggling to focus their auditory attention on a target audio source when they are attempting to do so can exhibit physical symptoms of frustration, aggravation, stress, discomfort, distraction or the like. For example, symptoms may include an increased heartrate or respiration rate, strained or distressed facial expressions, audial expressions (e.g., a gasp or a huff), sweating, fidgeting, drifting eye gaze or other such physical symptoms and expressions.

While the headphones 122 play the cocktail of sounds to the user 121, one or more sensors 130 disposed in the user's 121 environment can collect sensor data about the user such as for example but not limited to, images of facial expressions, body language and movements (e.g., nervous movements, gaze tracking, etc.), audio recordings of sounds (e.g., words, exasperations, etc.) and biometric readings (e.g., heartrate, respiration rate, temperature, etc.). According to some embodiments, the one or more sensors 130 can transmit these sensor readings to processing device 100. For example, in some embodiments, sensors 130 may be connected to and communicate with processing device 100 via the Internet (e.g., via a wired or Wi-Fi connection). According to some embodiments, sensors 130 can wirelessly communicate with a mobile application running on user device 121, which may transmit the sensor data to processing device 100.

According to some embodiments, the acceptance level determination engine 110 can be configured to determine an acceptance level of the user 121 based on the sensor data from the sensors 130. The acceptance level can represent the user's 121 tolerance of the current cocktail of sounds. In other words, the acceptance level can represent an estimation of how well the user 121 is able to focus on the primary audio source amidst the other background audio sources that are also being played to the user. If the user is having no trouble focusing on the primary audio source, the user's acceptance level will be high, whereas if the user 121 is struggling to focus on and/or follow along with the primary audio source, then the user's acceptance level will be lower. In some embodiments, the user's acceptance level can be considered to correspond to the user's level of frustration, agitation and/or distress, as indicated by the user's physical symptoms and expressions. According to some embodiments, the acceptance level determination engine 110 can determine an acceptance level of the user based on the sensor data obtained from sensors 130 using, for example, known techniques for determining the user's emotional state (e.g., as reflected by the user's expression, body language, audible expressions, heartrate or other such biological and/or biometric indications generated by the user). For example, a positive emotional state such as the user appearing to be happy or calm can indicate a high acceptance level, whereas a negative emotional state such as the user being angry or agitated can indicate a low acceptance level. As will be appreciated by those of skill in the art, known sensor-based emotion recognition techniques that utilize machine learning can determine the user's emotional state with sensor devices, cameras, microphones and other available technology by for example, determining the user's facial expressions, pupil dilation, heartrate, body language, audible sounds and other such indications of emotional state. In some embodiments, the acceptance level determination engine 110 can determine the acceptance level of the user based on one or more observed indications of emotional state (e.g., facial expression, heartrate, etc.). In some embodiments, the acceptance level determination engine 110 can determine a score that represents the user's acceptance level by observing and/or determining one or more indications of emotional state and applying an algorithm that determines a score for each (e.g., a smile may be assigned a default score of 90 whereas a frown has a default score of 30) and combining the scores into a weighted average representative of the acceptance level, which can be compared to one or more predetermined thresholds to determine how well the user is focusing on the target audio source. This data can be stored and tracked by the system to determine changes in the user over time. In some embodiments, the acceptance level can be represented numerically, such as a score out of a predetermined range (e.g., a number between 0 and 100), as a percentage or as a probability. In some embodiments, the acceptance level can be provided directly by user 121 as a user input into a mobile application running on the user device 120. For example, in some embodiments, the user device 120 can present user 121 with an interactive user interface that allows the user 121 to input an indication of how well the user 121 is currently able to focus on the primary audio source such as for example, a number on a scale of 1-10, selection of one of a plurality of buttons representing different levels of focus and/or agitation or any other such suitable user input. According to some embodiments, an acceptance level can be provided by a user of remote training device 140, such as by a teacher or parent observing the user 121 and observing signs of adequate focus or lack of acceptance.

As shown at block 206, the method includes determining (e.g., via processing system 100) how the user's 121 acceptance level compares to one or more predetermined thresholds to determine whether an adjustment should be made to the cocktail of sounds. For example, in some embodiments, if the acceptance level is below a first threshold, that can indicate that the user 121 is having trouble focusing on the primary audio source because of all of the background noise, in which case the method proceeds to block 208, at which point the method includes filtering (e.g., via processing system 100) one or more background audio sources from the current cocktail of sounds and/or reducing the volume of the one or more background audio sources played to the user 121 via the headphones 122. Similarly, according to some embodiments, if the if the acceptance level is above a second threshold, that can indicate that the user 121 is not having any trouble focusing on the primary audio source and could tolerate more background noise, in which case the method proceeds to block 210, at which point the method includes unfiltering (e.g., via processing system 100) one or more of the previously filtered background audio sources and/or increasing the volume of one or more of the currently unfiltered background audio sources played to the user 121 via the headphones 122. According to some embodiments if the acceptance level is between the first and second threshold, the method may take no action. In other words, in some embodiments, based on the current acceptance level of the user, the method may include increasing the background noise (i.e., increasing volume of current background audio sources and/or unfiltering of previously filtered background audio sources) to the cocktail of sounds if the user is not having any trouble focusing on the primary audio source, decreasing the background noise (i.e., decreasing volume of current background audio sources and/or filtering one or more currently playing background audio sources) of the cocktail of sounds if the user 121 cannot adequately focus on the primary audio source and/or leaving the level of background noise unchanged if the user 121 is handling the background noise moderately well.

According to some embodiments, the machine learning model 112 can receive the user's current acceptance level and data representative of each current audio source within the user's environment as inputs and output a background noise filtering adjustment. The background noise filtering adjustment can be an indication of whether one or more background audio sources should be added or removed from the cocktail of sounds and/or one or more of the background audio sources should have the volume adjusted. According to some embodiments, the background noise filtering adjustment can be received and processed by the audio source filtering engine 108 and/or the headphones 122 in order to provide the appropriate adjustment to the cocktail of sounds that are being played to the user 121 via the headphones 122. In some embodiments, the machine learning model 112 can compare the acceptance level to one or more predetermined threshold levels as described above. In some embodiments, the machine learning model 112 may not explicitly compare the acceptance level to predetermined thresholds but may use the acceptance level and current audio sources (both currently being played to the user 121 via headphones 122 and currently existing within the user's environment) as features of the machine learning model which are used to determine the output background noise filtering adjustment.

According to some embodiments, the process of presenting background noise to the user 121 via the headphones 122, determining the user's acceptance level and making adjustments to the background noise that is presented (i.e., unfiltered) to the user is performed iteratively to provide repeated updates to the audio sources and/or volumes of audio sources that are played to the user 121. In some embodiments, this iterative process can occur continuously, whereas in some embodiments the process can occur intermittently, such as for example, once every minute. As the audio sources that are played to the user change over time and as the user 121 develops their auditory attention abilities, the thresholds used to determine whether more or less background noise should be introduced (as embodied by the machine learning model 112) can dynamically change. Thus, over time, the machine learning model 112 can embody higher threshold levels based on a history of increasing tolerance to background noise exhibited by the user 121. According to some embodiments, the user's 121 profile data and progress (i.e., acceptance levels and/or indications of emotional state can be stored in relation to the specific sources of background noise that the user 121 was subjected to) can be indexed into a database and can be used for optimization.

As will be appreciated by those of skill in the art, in some embodiments, the machine learning model 112 can be trained to determine adjustments to the background noise presented to the user 121 that are designed to aid the user 121 in developing auditory attention abilities. For example, the machine learning model 112 can undergo a training phase that observes the nature of the current audio sources being played to the user 121 and the user's current acceptance level and tests different modifications to the background noise and observes the effect on the user's new acceptance level as well as overall improvements to the user's acceptance levels over time. In this way, the machine learning model 112 can learn how to best modify the background noise to help the user 121 improve and develop their own ability to naturally apply the cocktail effect. According to some embodiments, the machine learning model 112 can be trained with respect to the particular user 121, such that each different user 121 can have an individualized machine learning model 112 that is tailored to account for the individualized aspects of the user's audial sensitivities and learning style.

As will be appreciated by those of skill in the art, the phrase "machine learning" broadly describes a function of an electronic system that learns from data. A machine learning system, engine, or module can include a trainable machine learning algorithm that can be trained, such as in an external cloud environment, to learn currently unknown functional relationships between inputs and outputs.

Machine learning functionality can be implemented using an artificial neural network (ANN) that has the capability to be trained to perform a currently unknown function. In machine learning and cognitive science, ANNs are a family of statistical learning models inspired by the biological neural networks of animals, and in particular the brain. ANNs can be used to estimate or approximate systems and functions that depend on a large number of inputs.

ANNs can be embodied as so-called "neuromorphic" systems of interconnected processor elements that act as simulated "neurons" and exchange "messages" between each other in the form of electronic signals. Similar to the so-called "plasticity" of synaptic neurotransmitter connections that carry messages between biological neurons, the connections in ANNs that carry electronic messages between simulated neurons are provided with numeric weights that correspond to the strength or weakness of a given connection. The weights can be adjusted and tuned based at least in part on experience, making ANNs adaptive to inputs and capable of learning. For example, an ANN for handwriting recognition is defined by a set of input neurons that can be activated by the pixels of an input image. After being weighted and transformed by a function determined by the network's designer, the activation of these input neurons is then passed to other downstream neurons, which are often referred to as "hidden" neurons. This process is repeated until an output neuron is activated. The activated output neuron determines which character was read.

In certain embodiments of the invention, some or all of the processes performed by processing system 100 are performed by one or more specialized computers (e.g., one or more specialized processing units, a specialized computer with text data component, etc.) for carrying out defined tasks related to machine learning.

According to some embodiments, the machine learning model 112 can utilize a machine learning algorithm, such as a K-nearest neighbors (KNN) algorithm to determine a background noise filtering adjustment based on the current audio sources being played to the user, the user's current acceptance level and the available other background audio sources that are currently being filtered so that the user does not hear them. The filtering adjustment can be a selection of one or more audio sources to add (i.e., unfilter) or remove (i.e., filter) from the cocktail of sounds and/or a change in volume (i.e., up or down) to one or more audio sources in the cocktail of sounds. As will be appreciated by those of skill in the art, the machine learning model 112 can be trained using the features (e.g., frequency, tone, pitch, acoustic, visual, linguistic and any other suitable physical features.) of each audio source the user 121 is subjected to and the corresponding acceptance level of the user 121 to determine which sounds and combinations of sounds cause the user 121 to have difficulty in focusing on the primary audio source. The features can be represented as vectors of data indicative of an emotional response (e.g., data indicative of a facial expression, heartrate, etc.) in relation to the sounds played to the user in the cocktail of sounds. The model can then suggest changes to the cocktail of sounds being played to the user that are designed to maximize the amount of background noise being played to the user while maintaining a minimal level of auditory attention by the user 121 on the primary audio source (i.e., maintaining a minimum acceptance level). According to some embodiments, the machine learning model 112 can use a machine learning algorithm, such as a KNN algorithm to determine a frequency of how often new background sounds should be introduced to the user 121. As will be appreciated by those of skill in the art, a KNN algorithm utilizes knowledge of previous similar successful scenarios to decide how make changes to a current scenario. For example, the KNN algorithm can consider previous sounds generated from audio sources that were associated with a positive reaction (i.e., high acceptance) by the user to determine how to best make a change to the current cocktail of sounds to optimize the user's learning and experience with the goal of helping the user to achieve acceptance of typical background sounds while being able to maintain focus on a target audio source. The KNN algorithm described above is an example machine learning algorithm that can be used to generate a background noise filtering adjustment in accordance with some embodiments, but it is not intended to be limiting, as it is contemplated that various other machine learning algorithms such as regression analysis, Bayesian networks, Decision Tree, Particle Filter and other such machine learning algorithms could also be used. As will be appreciated by those of skill in the art, the particular machine learning algorithm(s) used in any particular embodiment can be selected based on the type of sensor data being collected and other factors deemed relevant.

The use of a machine learning model 112 to make determinations about modifying the nature of the background noise presented to the user 121 can eliminate the need for human oversight/intervention in aiding individuals with ADD or autism in developing auditory attention abilities and can also provide superior results by providing automated real-time adjustments to the cocktail of sounds presented to the individual that are tailored to the individual to attempt to maximize the individual's development of abilities.

Figure 3:
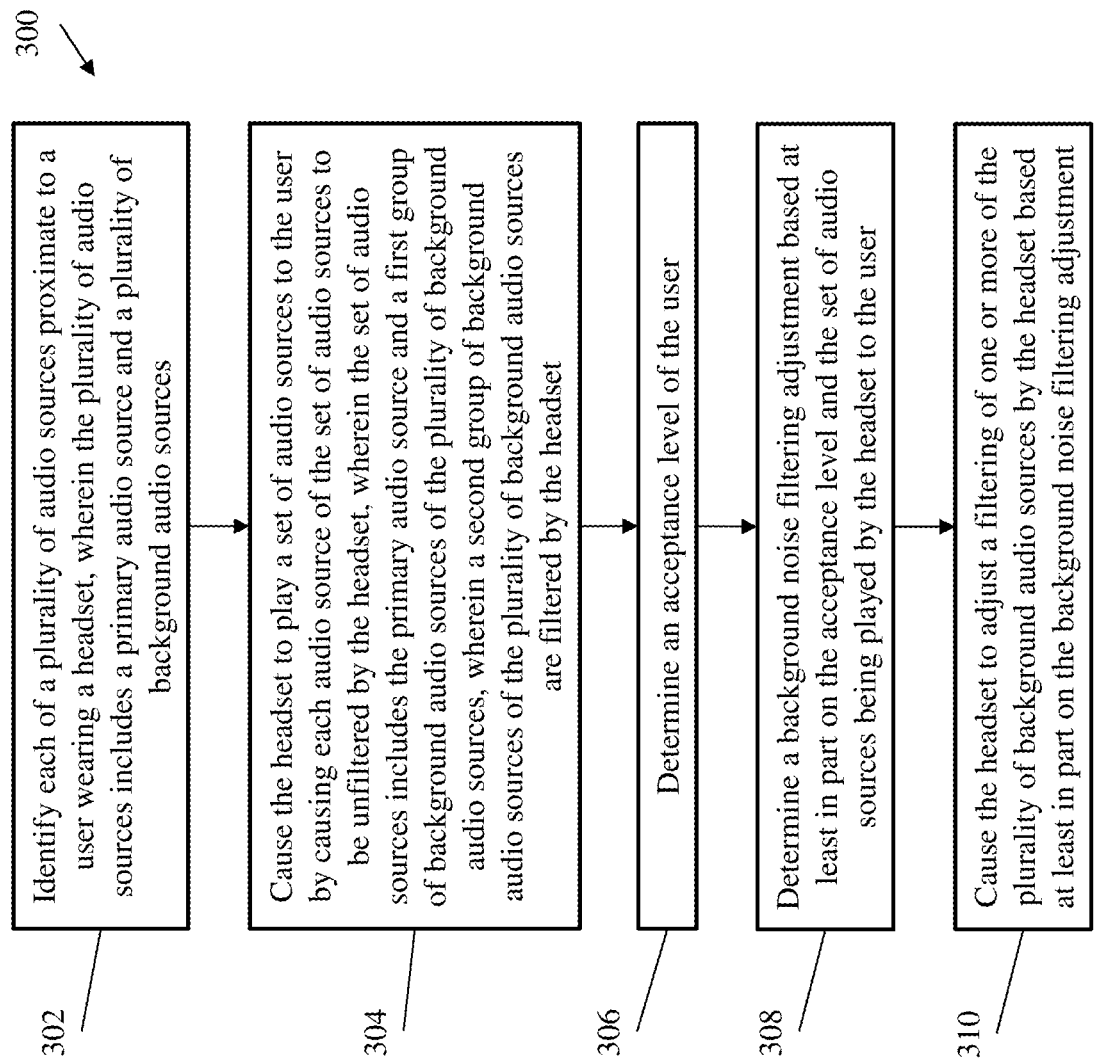
FIG. 3 illustrates a flow diagram of another process for automatically aiding an individual with developing auditory attention abilities in accordance with one or more embodiments of the present invention.

Turning now to FIG. 3, a flow diagram of another method 300 for automatically aiding an individual with developing auditory attention abilities in accordance with an embodiment is shown. In one or more embodiments of the present invention, the method 300 may be embodied in software that is executed by computer elements located within a network that may reside in the cloud, such as the cloud computing environment 50 described herein above and illustrated in FIGS. 4 and 5. In other embodiments, the computer elements may reside on a computer system or processing system, such as the processing system 100 described herein above and illustrated in FIG. 1, processing system 600 described herein above and illustrated in FIG. 6, or in some other type of computing or processing environment.

The method 300 begins at block 302 and includes identifying (e.g., via processing device 100) each of a plurality of audio sources proximate to a user wearing a headset (e.g., headphones 122). According to some embodiments, the plurality of audio sources include a primary audio source and a plurality of background audio sources, that can be identified by audio source identification engine 106 as described previously above. According to some embodiments, audio sources proximate to a user can refer to audio sources that are generally within ear shot of the user. According to some embodiments, proximate audio sources can include audio sources that are for example, detectable by a microphone of user device 121 or a microphone associated with headphones 122. In some embodiments, proximate audio sources can include any audio source that is detectable by a sensor 130 disposed in the user's environment (e.g., such as microphones positioned around a classroom). According to some embodiments, proximate audio sounds can be audio sounds that are detectable by a microphone of user device 121 that have a volume that is higher than a predetermined threshold level of volume, such as 0 dB, 10 dB, 20 dB or any other such threshold level of volume as may be selected by a user.

As shown at block 304, the method includes causing (e.g., via processing device 100) the headset to play a set of audio sources to the user by causing each audio source of the set of audio sources to be unfiltered by the headset, such that the audio sources "pass through" the headset and the user can hear them. The set of audio sources includes the primary audio source (e.g., a teacher's voice) and a first group of background audio sources (e.g., the voices of students 1, 2 and 3) of the plurality of background audio sources (e.g., the voices of students 1-10). A second group of background audio sources of the plurality of background audio sources are filtered by the headset (e.g., the voices of students 4-10), such that the user wearing the headset cannot hear them. In other words, the primary audio source and some of the background audio sources can be presented to the user in a cocktail of sounds, whereas the remaining background audio sources are filtered/canceled by the headset so that the user cannot hear them.

According to some embodiments, causing the headset to play a set of audio sources to the user includes selecting one or more of the background sounds as the first group of background audio sources using a machine learning model and based on the plurality of background audio sources. In other words, a machine learning model (e.g., machine learning model 112) can receive all of the audio sources present in the environment (including the primary audio source) and determine a set of initial background audio sources to present to the user along with the primary audio source. As described above, in some embodiments, the machine learning model can be trained to be personalized to the individual user to better determine the initial conditions. For example, the machine learning model may incorporate knowledge that this particular user has extreme difficulty in focusing on a primary audio source when there are high-pitched voices present in the cocktail of noises, and therefore, the machine learning model may filter all high-pitched voices from the initial set of sounds presented to the user and attempt to slowly introduce them while monitoring the user for acceptance.

As shown at block 306, the method includes determining (e.g., via processing device 100) an acceptance level of the user. According to some embodiments, determining the acceptance level of the user includes obtaining sensor data from one or more sensors proximate the user, the sensor data being representative of observations about the user and determining an emotional state, state of agitation, or any other such state of the user that may indicate a lack of focus on the primary audio source, based on the sensor data using known techniques such as for example, sensor-based emotion recognition using machine learning algorithms. For example, if the user has an increased heartrate, a distressed facial expression and/or is heard making sounds of exasperation, those can be indications that the user is struggling to focus on the primary audio source. In some embodiments, obtaining sensor data from one or more sensors proximate the user can include one or more of obtaining images of the user from an image capture device, obtaining audio data of noises made by the user from a microphone and obtaining biometric data of the user from a biometric sensor (e.g., a wearable smartwatch). According to some embodiments, an acceptance level can be determined algorithmically based on a comparison of one or more observed metrics (e.g., heart rate, respiration rate, etc.) to baseline readings. In some embodiments, known techniques of applying artificial intelligence to analyze facial expressions, body language, movements and sounds of the user 121 to determine the user's state can also be used. It will be understood that the foregoing are merely examples and many other types of sensors can be used to obtain visual, audial and biometric data from the user that can be used to determine the user's state. According to some embodiments, determining an acceptance level of the user comprises receiving a user-input indication of a degree to which the user is able to focus on the primary audio source being played by the headset from an input device proximate the user. For example, a user may input an indication of their level of agitation/focus via a mobile application running on a mobile device possessed by the user.

As shown at block 308, the method includes determining (e.g., via processing device 100) a background noise filtering adjustment on the acceptance level and the set of audio sources being played by the headset to the user. According to some embodiments, the background noise filtering adjustment can be determined by a user input (e.g., at the direction of a user of remote training device 140). In some embodiments, the background noise filtering adjustment can be determined in accordance with a predetermined set of rules. In some embodiments, the background noise filtering adjustment can be determined using a machine learning model (e.g., machine learning model 112). For example, if the user has a low level of acceptance, the machine learning model may determine to reduce the volume of one or more of the background audio sources being played to the user or filter them so that the user cannot hear them. Conversely, if the user has a high level of acceptance, the machine learning model may determine that the user can tolerate more background noise and may determine to turn up the volume of one or more background audio sources being played to the user or introduce new ones. In this way, the machine learning model can also base the background noise filtering adjustment on background audio sources that are present in the user's environment but that are currently being filtered such that the user cannot hear them. According to some embodiments, the background noise filtering adjustment determined by the machine learning model can be individualized to the particular user based on the training of the machine learning model. As will be appreciated, different people can have different audial sensitivities and may process different sounds differently. So, for example, a machine learning model trained to aid a particular individual may embody knowledge that the individual is not distracted by certain types of sounds (e.g., certain frequencies), but finds a combination of particular types of sounds particularly distracting (e.g., a dog barking and music playing at the same time), whereas other individuals are affected differently by these same noises. Thus, the machine learning model can provide intelligent, customized responses to better aid in a particular user's development of auditory attention abilities.

According to some embodiments, the background noise filtering adjustment can be an instruction to move one or more background audio sources of the plurality of background audio sources from the first group of background audio sources to the second group of background audio sources to reduce a total amount of background noise played by the headset to the user and/or an instruction to move one or more background audio sources of the plurality of background audio sources from the second group of background audio sources to the first group of background audio sources to increase a total amount of background noise played by the headset to the user. In other words, the background noise filtering adjustment can be an instruction to add and/or remove (i.e., unfilter and/or filter) selected background audio sources from/to the cocktail of sounds presented to the user and/or adjust the volumes of selected current background audio sources.

According to some embodiments, the machine learning model is configured to iteratively determine a new background noise filtering adjustment based on an updated acceptance level that is determined in response to an adjustment made to the filtering of one or more of the plurality of background audio sources by the headset based on a previous background noise filtering adjustment. In some embodiments, the machine learning model is trained to determine one or more background noise filtering adjustments that are particular to the user. Thus, in some embodiments, the method 300 can include training the machine learning model.

According to some embodiments, training the machine learning model includes playing a test primary audio source to the user and determining a change in the user's acceptance level in response to variably introducing a plurality of test background audio sources to the user. In some embodiments, one or more of the plurality of test background audio sources can include artificial audio sources. For example, data store 124 can store a repository of pre-recorded sounds and noises that can be selectively played to the user during a training phase to observe the effect on the user. Thus, noises having different characteristics (e.g., frequency, tempo, volume, etc.) can be tested on the user and tested in different combinations to determine how the noises impact the user's ability to focus on the primary audio source.

As shown at block 310, the method includes causing (e.g., via processing device 100) the headset to adjust a filtering of one or more of the plurality of background audio sources by the headset based on the background noise filtering adjustment. In other words, in some embodiments, the processing system 100 can direct the headset (e.g., headphones 122) to filter or unfilter one or more selected audio sources and/or increase and/or reduce the volume of one or more audio sources currently being played to the user.

Additional processes may also be included. It should be understood that the processes depicted in FIGS. 2 and 3 represent illustrations, and that other processes may be added or existing processes may be removed, modified, or rearranged without departing from the scope and spirit of the present disclosure.

Figure 4:
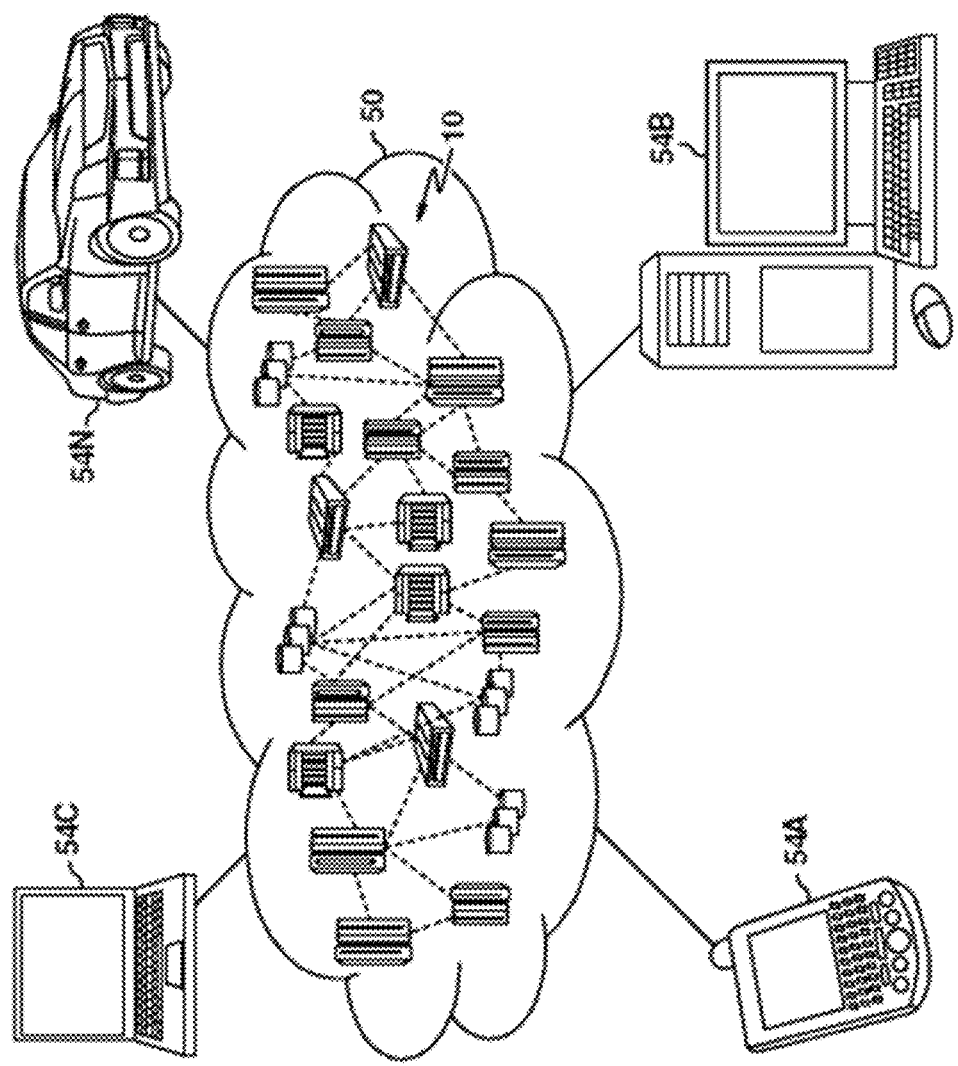
FIG. 4 illustrates a cloud computing environment according to one or more embodiments of the present invention.
Figure 5:
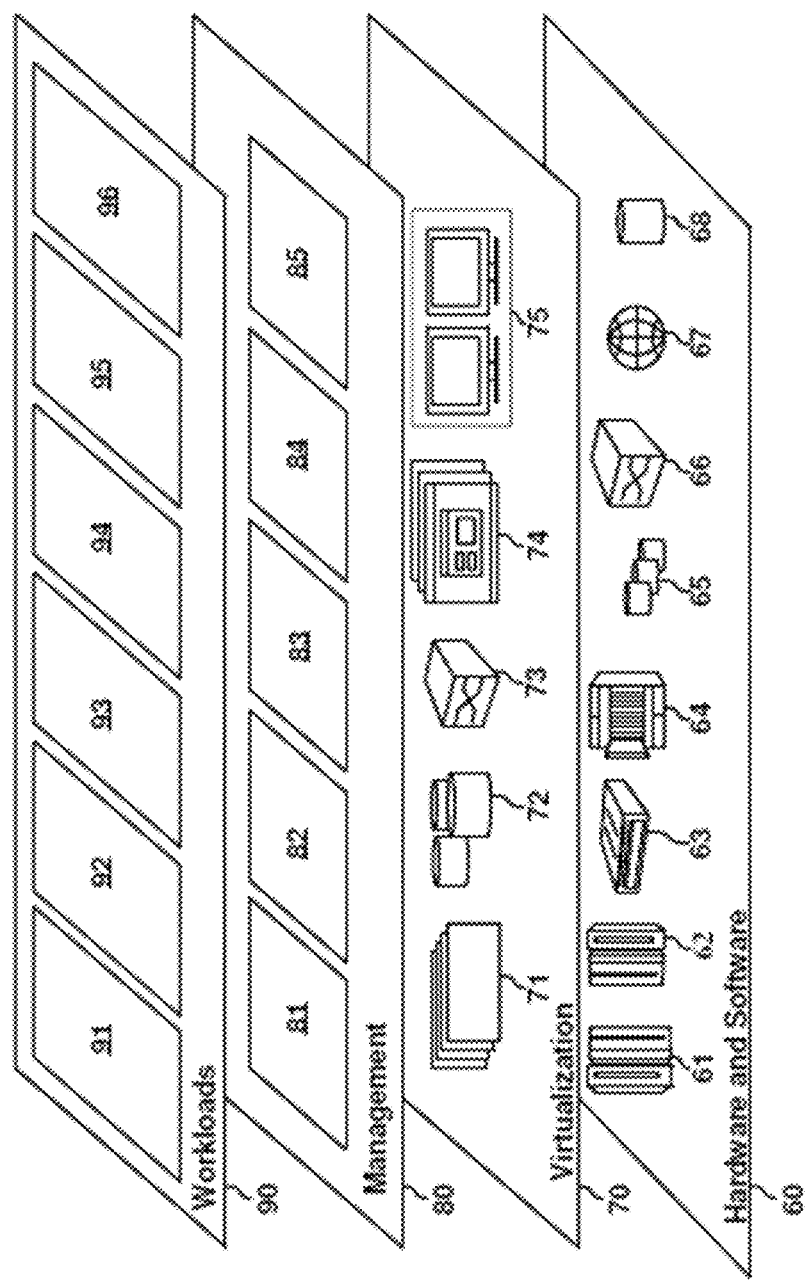
FIG. 5 illustrates abstraction model layers according to one or more embodiments of the present invention.

FIG. 4 depicts a cloud computing environment according to one or more embodiments of the present invention. FIG. 5 depicts abstraction model layers according to one or more embodiments of the present invention.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and automatically aiding an individual with developing auditory attention abilities 96.

FIG. 6 depicts a processing system for implementing one or more embodiments of the present invention. It is understood that one or more embodiments of the present invention are capable of being implemented in conjunction with any other type of computing environment now known or later developed. For example, FIG. 6 depicts a block diagram of a processing system 600 for implementing the techniques described herein. In accordance with one or more embodiments of the present invention, system 600 and/or processing system 100 is an example of a cloud computing node 10 of FIG. 4. In the embodiment shown in FIG. 6, processing system 600 has one or more central processing units (processors) 21a, 21b, 21c, etc. (collectively or generically referred to as processor(s) 21 and/or as processing device(s)). According to one or more embodiments of the present invention, each processor 21 can include a reduced instruction set computer (RISC) microprocessor. Processors 21 are coupled to system memory (e.g., random access memory (RAM) 24) and various other components via a system bus 33. Read only memory (ROM) 22 is coupled to system bus 33 and can include a basic input/output system (BIOS), which controls certain basic functions of processing system 600.

Further illustrated are an input/output (I/O) adapter 27 and a communications adapter 26 coupled to system bus 33. I/O adapter 27 can be a small computer system interface (SCSI) adapter that communicates with a hard disk 23 and/or a tape storage drive 25 or any other similar component. I/O adapter 27, hard disk 23, and tape storage device 25 are collectively referred to herein as mass storage 34. Operating system 40 for execution on processing system 600 can be stored in mass storage 34. The RAM 24, ROM 22, and mass storage 34 are examples of memory 19 of the processing system 600. A network adapter 26 interconnects system bus 33 with an outside network 36 enabling the processing system 600 to communicate with other such systems.

A display (e.g., a display monitor) 35 is connected to system bus 33 by display adaptor 32, which can include a graphics adapter to improve the performance of graphics intensive applications and a video controller. According to one or more embodiments of the present invention, adapters 26, 27, and/or 32 can be connected to one or more I/O busses that are connected to system bus 33 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 33 via user interface adapter 28 and display adapter 32. A keyboard 29, mouse 30, and speaker 31 can be interconnected to system bus 33 via user interface adapter 28, which can include, for example, a Super I/O chip integrating multiple device adapters into a single integrated circuit.

According to one or more embodiments of the present invention, processing system 600 includes a graphics processing unit 37. Graphics processing unit 37 is a specialized electronic circuit designed to manipulate and alter memory to accelerate the creation of images in a frame buffer intended for output to a display. In general, graphics processing unit 37 is very efficient at manipulating computer graphics and image processing and has a highly parallel structure that makes it more effective than general-purpose CPUs for algorithms where processing of large blocks of data is done in parallel.

Thus, as configured herein, processing system 600 includes processing capability in the form of processors 21, storage capability including system memory (e.g., RAM 24), and mass storage 34, input means such as keyboard 29 and mouse 30, and output capability including speaker 31 and display 35. According to one or more embodiments of the present invention, a portion of system memory (e.g., RAM 24) and mass storage 34 collectively store an operating system such as the AIX® operating system from IBM Corporation to coordinate the functions of the various components shown in processing system 600.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
identifying each of a plurality of audio sources detectable by a microphone of a headset worn by a user, wherein the plurality of audio sources comprises a primary audio source and a plurality of background audio sources;
causing the headset to play a set of audio sources to the user by causing each audio source of the set of audio sources to be unfiltered by the headset, wherein the set of audio sources comprises the primary audio source and a first group of background audio sources of the plurality of background audio sources, and wherein a second group of background audio sources of the plurality of background audio sources are filtered by the headset;
determining an acceptance level of the user, the determining an acceptance level of the user comprising receiving, from a mobile application running on a mobile device, a user-input indication of a degree to which the user is able to focus on the primary audio source currently being played by the headset, the user-input indication input by the user into the mobile application via a selection button of a user interface of the mobile application;
determining, based at least in part on the acceptance level and the set of audio sources being played by the headset to the user, a background noise filtering adjustment; and
causing, based at least in part on the background noise filtering adjustment, the headset to adjust a filtering of one or more of the plurality of background audio sources by the headset.

2. The computer-implemented method of claim 1, wherein causing the headset to play the set of audio sources to the user comprises:
selecting, using a machine learning model and based at least in part on the plurality of background audio sources, one or more of the background audio sources as the first group of background audio sources.

3. The computer-implemented method of claim 2, wherein the machine learning model is configured to iteratively determine a new background noise filtering adjustment based at least in part on an updated acceptance level that is determined in response to an adjustment made to the filtering of one or more of the plurality of background audio sources by the headset based on a previous background noise filtering adjustment.

4. The computer-implemented method of claim 3, wherein the machine learning model is trained to determine one or more background noise filtering adjustments that are particular to the user.

5. The computer-implemented method of claim 4, wherein training the machine learning model comprises:
playing a test primary audio source to the user; and
responsive to variably introducing a plurality of test background audio sources to the user, determining a change in the acceptance level of the user, wherein one or more of the plurality of test background audio sources comprise artificial audio sources.

6. The computer-implemented method of claim 1, wherein the background noise filtering adjustment comprises an instruction to move one or more background audio sources of the plurality of background audio sources from the first group of background audio sources to the second group of background audio sources to reduce a total amount of background noise played by the headset to the user.

7. The computer-implemented method of claim 1, wherein the background noise filtering adjustment comprises an instruction to move one or more background audio sources of the plurality of background audio sources from the second group of background audio sources to the first group of background audio sources to increase a total amount of background noise played by the headset to the user.

8. The computer-implemented method of claim 1, wherein determining the acceptance level of the user comprises:
    obtaining sensor data from one or more sensors, the sensor data being representative of observations about the user; and
    determining, based on the sensor data, an emotional state of the user.

9. The computer-implemented method of claim 8, wherein obtaining sensor data from one or more sensors comprises one or both of:
    obtaining images of the user from an image capture device; and
    obtaining biometric data of the user from a biometric sensor.

10. A system comprising:
    a memory having computer readable instructions; and
    one or more processors for executing the computer readable instructions, the computer readable instructions controlling the one or more processors to perform operations comprising:
        identifying each of a plurality of audio sources detectable by a microphone of a headset worn by a user, wherein the plurality of audio sources comprises a primary audio source and a plurality of background audio sources;
        causing the headset to play a set of audio sources to the user by causing each audio source of the set of audio sources to be unfiltered by the headset, wherein the set of audio sources comprises the primary audio source and a first group of background audio sources of the plurality of background audio sources, and wherein a second group of background audio sources of the plurality of background audio sources are filtered by the headset;
        determining an acceptance level of the user, the determining an acceptance level of the user comprising receiving, from a mobile application running on a mobile device, a user-input indication of a degree to which the user is able to focus on the primary audio source currently being played by the headset, the user-input indication input by the user into the mobile application via a selection button of a user interface of the mobile application;
        determining, based at least in part on the acceptance level and the set of audio sources being played by the headset to the user, a background noise filtering adjustment; and
        causing, based at least in part on the background noise filtering adjustment, the headset to adjust a filtering of one or more of the plurality of background audio sources by the headset.

11. The system of claim 10, wherein causing the headset to play the set of audio sources to the user comprises:
    selecting, using a machine learning model and based at least in part on the plurality of background audio sources, one or more of the background audio sources as the first group of background audio sources.

12. The system of claim 11, wherein the machine learning model is configured to iteratively determine a new background noise filtering adjustment based at least in part on an updated acceptance level that is determined in response to an adjustment made to the filtering of one or more of the plurality of background audio sources by the headset based on a previous background noise filtering adjustment.

13. The system of claim 12, wherein the machine learning model is trained to determine one or more background noise filtering adjustments that are particular to the user.

14. The system of claim 13, wherein training the machine learning model comprises:
    playing a test primary audio source to the user; and
    responsive to variably introducing a plurality of test background audio sources to the user, determining a change in the acceptance level of the user, wherein one or more of the plurality of test background audio sources comprise artificial audio sources.

15. The system of claim 10, wherein the background noise filtering adjustment comprises an instruction to move one or more background audio sources of the plurality of background audio sources from the first group of background audio sources to the second group of background audio sources to reduce a total amount of background noise played by the headset to the user.

16. A computer program product comprising a computer readable storage medium having program instructions embodied therewith, the program instructions executable by a computer processor to cause the computer processor to perform a method comprising:
    identifying each of a plurality of audio sources detectable by a microphone of a headset worn by a user, wherein the plurality of audio sources comprises a primary audio source and a plurality of background audio sources;
    causing the headset to play a set of audio sources to the user by causing each audio source of the set of audio sources to be unfiltered by the headset, wherein the set of audio sources comprises the primary audio source and a first group of background audio sources of the plurality of background audio sources, and wherein a second group of background audio sources of the plurality of background audio sources are filtered by the headset;
    determining an acceptance level of the user, the determining an acceptance level of the user comprising receiving, from a mobile application running on a mobile device, a user-input indication of a degree to which the user is able to focus on the primary audio source currently being played by the headset, the user-input indication input by the user into the mobile application via a selection button of a user interface of the mobile application;
    determining, model based at least in part on the acceptance level and the set of audio sources being played by the headset to the user, a background noise filtering adjustment; and
    causing, based at least in part on the background noise filtering adjustment, the headset to adjust a filtering of one or more of the plurality of background audio sources by the headset.

17. The computer program product of claim 16, causing the headset to play the set of audio sources to the user comprises:
  selecting, using a machine learning model and based at least in part on the plurality of background audio sources, one or more of the background audio sources as the first group of background audio sources.

18. The computer program product of claim 17, wherein the machine learning model is configured to iteratively determine a new background noise filtering adjustment based at least in part on an updated acceptance level that is determined in response to an adjustment made to the filtering of one or more of the plurality of background audio sources by the headset based on a previous background noise filtering adjustment.

19. The computer program product of claim 18, wherein the machine learning model is trained to determine one or more background noise filtering adjustments that are particular to the user.

* * * * *